(12) United States Patent
Eckert et al.

(10) Patent No.: US 7,691,372 B2
(45) Date of Patent: Apr. 6, 2010

(54) USE OF ANTIBODIES FOR THE VACCINATION AGAINST CANCER

(75) Inventors: Helmut Eckert, Oberwil (CH); Hans Loibner, Vienna (AT)

(73) Assignee: Igeneon Krebs-Immuntherapie Forschungs-und Entwickungs-AG, Vienna (AT)

( * ) Notice: Subject to any disclaimer, the term of this patent is extended or adjusted under 35 U.S.C. 154(b) by 0 days.

(21) Appl. No.: 11/548,269

(22) Filed: Oct. 10, 2006

(65) Prior Publication Data
US 2007/0224202 A1    Sep. 27, 2007

Related U.S. Application Data

(63) Continuation of application No. 09/889,300, filed on Sep. 13, 2001, now abandoned.

(51) Int. Cl.
A61K 39/395    (2006.01)
(52) U.S. Cl. .................................................. 424/130.1
(58) Field of Classification Search ............... 424/130.1
See application file for complete search history.

(56) References Cited

U.S. PATENT DOCUMENTS

| | | | |
|---|---|---|---|
| 5,270,202 A | 12/1993 | Raychaudhuri | |
| 5,863,538 A * | 1/1999 | Thorpe et al. ............. | 424/136.1 |
| 6,051,230 A * | 4/2000 | Thorpe et al. ............. | 424/178.1 |
| 6,235,280 B1 | 5/2001 | Chatterjee et al. | |
| 6,632,431 B2 | 10/2003 | Wu | |

FOREIGN PATENT DOCUMENTS

| | | |
|---|---|---|
| WO | WO-96 01126 | 1/1996 |
| WO | WO-97 15597 | 5/1997 |
| WO | WO-98 56416 | 12/1998 |
| WO | WO-98 56419 | 12/1998 |
| WO | WO-99 65523 | 12/1999 |

OTHER PUBLICATIONS

Jain (Scientific American Jul. 1994).*
Dillman (Annals of Internal Medicine, vol. 111, pp. 592-603, 1989).*
Campbell (Monoclonal Antibody Technology; Elsevier Science Publication Company Inc: pp. 1-33).*
Gupta (Advanced Drug Delivery Reviews 1998; 32:155-172).*
Campbell (Monoclonal Antibody Technology; Elsevier Science Publication Company Inc: pp. 1-33, 1986).*
Pervin S et al., "Proliferation of T-cells from colon cancer patients by peptides based on the structure of an anti-idiotype antibody mimicking CEA," #3231. XP-002076985.
Fagerberg et al., "Tumor Regression in Monoclonal Antibody-treated Patients Correlates with the Presence of Anti-Idiotype-reactive T Lymphocytes" Cancer Research, vol. 55, May 1, 1995, pp. 1824-1827.
Leveugle B et al., "PSA-directed immunotherapy of prostate cancer," #2424. XP-002117652.
Chakroaborty M et al., "Immune responses in advanced breast cancer patients treated with an anti-idiotype antibody vaccine," #4139. XP-002076982.
Katayama M et al., "Expression of neural cell adhesion molecule L2 in human lung cancer cell lines," XP-002255877.
Rao, Yong et al., "Indentification of a peptide sequence . . . ," The Journal of Cell Biology, vol. 118, No. 4, Aug. 1992, pp. 937-949.
Zola, Heddy et al., *Monoclonal Antibodies A Manual of Techniques*, CRC Pres, c1987, Boca Raton, FL., pp. 23-61.
Litvinov, Sergey V. et al., "Ep-cam: a human epithelial antigen . . . ," The Journal of Cell Biology, vol. 125, 1994, pp. 437-446.
Miyake, Masayuki et al., "Correlation of Expression . . . ," The New England Journal of Medicine, vol. 327, No. 1, pp. 14-18.
Koprowski, Hilary at al., "Human anti-idiotype antibodies . . . ," Proc. Natl. Acad. Sci., vol. 81, Jan. 1984, pp. 216-219.
Devita, Vincent T. Jr. et al., *Biologic Therapy of Cancer*, 2nd Edition, c1995, Philadelphia, J.B. Lippincott Company, pp. 53-86.
Fagerberg, Jan et al., "Humoral anti-Idiotypic and anti-anti-idiotypic . . . ," Cancer Immunol Immunother, 1996, 42, pp. 81-87.
Benchimol, Sarita et al., "Carcinoembyonic antigen, a human tumor . . . ," Cell, vol. 57, Apr. 21, 1989, pp. 327-334P.
Evans et al. Q J Med 1999; 92:299-307.
Braun et al. Clinical Cancer Research Dec. 1999; 5:3999-4004.
Pardoll D Immunology Today 1993;14(6):310-316.
Hayden et al., "Antibody Engineering," Current Opinion in Immunology, vol. 9, 1997, pp. 201-212.
Cirulli et al., "KSA Antigen Ep-CAM Mediates Cell-Cell Adhesion of Pancreatic . . . ," The Journal of Cell Biology, vol. 140, 1998, pp. 1519-1534.
Strnad et al., "Molecular Cloning and Characterization of a Human . . . ," Cancer Research, vol. 49, Jan. 15, 1989, pp. 314-317.
Herlyn et al., "IgG2a monoclonal antibodies inhibit human . . . ," Proc. Natl. Acad. Sci. USA, vol. 79, Aug. 1982, pp. 4761-4765.
Ross et al., "Isolation and Characterization of a Carcinoma-Associated Antigen," Biochemical and Biophysical Research Communications, vol. 135, No. 1, 1986, pp. 297-303.
Sears et al. "Phase II Clinical trial of a Murine . . . ," Cancer Research, vol. 45, Nov. 1985, pp. 5910-5913.
Sears et al., "Effects of Monoclonal Anitbody Immunotherapy . . . ," J. Biol. Resp. Modif., vol. 3, No. 2, 1984, pp. 138-150.
Samonigg at al., "Immune Response to Tumor Antigens . . . ," Clinical Immunology and Immunopathology, vol. 66, No. 3, Dec. 1992, pp. 271-277.
Balzer et al. (J. Mol Med 1999;77:699-713).
Gura (Science, v278, 1997, pp. 1041-1042).
Ragnhammar et al. (Med Onool & Tumor Pharacother 1993; 10(1/2):61-70).

(Continued)

*Primary Examiner*—Christopher H Yaen
(74) *Attorney, Agent, or Firm*—Birch, Stewart, Kolasch & Birch, LLP

(57) ABSTRACT

Described is the use of antibodies which are directed against human cellular membrane antigens for the vaccination against cancer diseases.

19 Claims, 13 Drawing Sheets

OTHER PUBLICATIONS

Weiner, L.M. et al., "Antibody delivery and effector cell activation in a phase II . . . ," Cancer Research, May 1, 1998, 48, pp. 2568-2573.

Herlyn, D. et al., "Immunomodulatory activity of monoclonal anti-idiotypic antibody . . . ," Journal of Immunotherapy, 1994, 15, pp. 303-311.

Ragnhammar, P. et al., "Granulocyte/macrophage-colony-stimulating factor augments . . . ," Cancer Immunol Immunother. Jun. 1995, 40(6), pp. 367-375.

Ragnhammar, P. et al., "Effect of monoclonal antibody 17-1A and GM-CSF in patients . . . ," Int. J. Cancer, 1993, 53, pp. 751-758.

Elias, D.J. et al., "Monoclonal antibody KS1/4-methotrexate immonoconjugate studies . . . ," Am J Resir Crit Care Med, 1994, vol. 150, pp. 1114-1122.

Reithmuller, G. et al., "Randomised trial of monoclonal antibody for adjuvant therapy . . . ," The Lancet, vol. 343, May 14, 1994, pp. 1177-1183.

Weiner L.M., Seminars Oncology, vol. 26, No. 4, Suppl 12, pp. 41-50, 1999.

* cited by examiner

SW2 cells in medium with 100 µg/ml HE2, hour 0

SW2 cells in medium with 100 µg/ml, hour 4

SW2 cells in medium, hour 0

SW2 cells in medium, hour 4

Figure 3

**Vaccination of goats with HE2-F(ab)'2:
Serum Ig with specificity for HE2**

Vaccination of goats with HE2-F(ab)'2: Binding of serum Ig to Ep-CAM positive human stomach cancer cells (KATO III)

Vaccination of goats with HE2-F(ab)'2:
Binding of serum Ig to Ep-CAM negative
human melanoma cells (WM9)

Vaccination of goats with HE2-F(ab)'2:
Binding of affinity-purified serum Ig to Ep-CAM negative human melanoma cells

Vaccination of a patient with intestinal cancer with HE2: Induction of antibodies against human stomach cancer cells (KATO III)

Vaccination of a patient with intestinal cancer with HE2:
Induction of serum cytotoxicity against human
stomach cancer cells (KATO III)

USE OF ANTIBODIES FOR THE VACCINATION AGAINST CANCER

CROSS REFERENCE TO RELATED APPLICATIONS

This application is a Continuation of application Ser. No. 09/889,300 filed on Sep. 13, 2001 now abandoned the entire contents of which are hereby incorporated by reference and for which priority is claimed under 35 U.S.C. §120.

The present invention relates to the use of antibodies which are directed against human cellular membrane antigens for the preparation of a pharmaceutical composition for the vaccination against cancer.

With the discovery of the hybridoma technology it became possible to generate monoclonal antibodies (MAB) against the most varied antigens. This technology which can generally be applied to all biological problems also plays an important role in cancer research. Over the last twenty years MAB directed against a multitude of tumor-associated antigens (TAA) have been produced. TAA are structures which are expressed predominantly on the cell membrane of tumor cells and which, thus, allow differentiation from non-malignant tissue. Therefore, they are regarded as targets for diagnostic or therapeutic applications on the basis of specific MAB or derivatives derived from these MAB.

Direct therapeutic applications of MAB which are directed against TAA are based on passive immunotherapies, i.e. an MAB or a derivative is applied systemically to cancer patients in a suitable amount and has a therapeutic effect only as long as the concentration in the organism is sufficiently high. The biological half-life of such agents depends on their structure and ranges from only a few hours to several days. It is therefore necessary to repeat the applications. However, if xenogenic antibodies (e.g. murine MAB) are used, this leads to unwanted immune reactions, which can lead to the neutralization of a possible therapeutic effect and to dangerous side effects (anaphylactic shock). Therefore, such immunotherapeutics can only be administered for a limited period of time.

Another approach for the immunotherapy of cancer is based on the selective activation of the immune system of cancer patients so as to combat malignant cells for which the most varied types of cancer vaccines are used. These include vaccinations with autologous or allogenic tumor cells, vaccinations with autologous or allogenic tumor cells which have been chemically modified or which have been modified by gene technological techniques, vaccinations with isolated TAA or TAA which have been produced using chemical or gene technological methods, with peptides derived therefrom, and, recently, also vaccinations with DNAs coding for TAA or structures derived therefrom, etc. An alternative method is based on the use of anti-idiotypic antibodies for the vaccination against cancer. Suitable anti-idiotypic antibodies can immunologically mimic a TAA. As xenogeneic proteins (e.g. murine antibodies, goat antibodies etc.) they induce a strong immune response in human after vaccination—in contrast to the proper human tumor antigens, which, as structures of the self, are often immunogenic to a low degree only. Therefore, anti-idiotypic antibodies can be used for vaccination as an immunogenic substitute for a tumor antigen.

In contrast to the passive immunotherapy with anti-tumor antibodies in the active specific cancer immunotherapy, even very small amounts of a suitable vaccine are, in principle, sufficient to induce an immunity which lasts for months or for years and which can be boosted by repeated vaccinations if it weakens. Moreover, active immunization allows to induce a humoral as well as a cellular immunity the cooperation of which can lead to an effective protection.

In summary, the use of antibodies or their derivatives for immunotherapy against cancer, which has been described so far, is essentially based on two principles:
 passive therapy with antibodies or their derivatives which are directed against TAA.
 active immunization (vaccination) with antibodies or their derivatives which are directed against the idiotype of antibodies having a specificity against TAA.

In the course of the discovery and the subsequent characterization of the most varied TAA, it has turned out that they have important functions as regards cancer cells. They enable the degenerate cells to show properties characteristic of the malignant phenotype, such as an increased capability for adhesion, which play an important role in establishing metastases. However, such antigens can, at certain stages, also be expressed on normal cells where they are responsible for the normal functions of these cells. Without laying claim to completeness, some examples of such antigens are listed in the following:
 N-CAM (Neuronal Cell Adhesion Molecule), which is often expressed on tumors of neuronal origin and which effects homophilic adhesion (J. Cell Biol. 118 (1992), 937).
 The Lewis Y carbohydrate antigen, which occurs on the majority of tumors of epithelial origin, but which also plays an important role during the fetal development of epithelial tissues. It has been shown that the expression of this antigen in lung cancer is strongly associated with an unfavorable prognosis since Lewis Y positive cancer cells obviously have a higher metastatic potential (N. Engl. J. Med. 327 (1992), 14).
 CEA (Carcino Embryonic Antigen), which often occurs on epithelial tumors of the gastrointestinal tract and which has been identified as a self-adhesion molecule (Cell 57 (1989), 327).
 Ep-CAM (Epithelial Cell Adhesion Molecule), which is expressed on nearly all tumors of epithelial origin, but which also occurs on a large number of normal epithets. It has been characterized as a self-adhesion molecule and can therefore be classified as a pan-epithelial adhesion antigen (J. Cell Biol. 125 (1994), 437).

The technical problem underlying the present invention is to provide further means and methods which allow an efficient prophylaxis against or therapy of cancer diseases.

This problem has been solved by the provision of the embodiments as characterized in the claims.

Accordingly, the invention relates to the use of antibodies which are directed against human cellular membrane antigens for the preparation of a pharmaceutical composition for the prophylactic and/or therapeutic vaccination against cancer. In this context the term "cellular membrane antigens" relates to structures which are presented on the cell membrane of cells. These include in particular receptors, such as the transferrin receptor, or other molecules, such as E cadherine or Ep-CAM.

In a preferred embodiment, such a cellular membrane antigen is a tumor-associated antigen. In this context, the term "tumor-associated antigen" means a structure which is predominantly presented by tumor cells and thereby allows a differentiation from non-malignant tissue. Preferably, such a tumor-associated antigen is located on or in the cell membrane of a tumor cell. This does, however, not exclude the possibility that such antigens also occur on non-degenerate cells. The tumor-associated antigens can, for example, be polypeptides, in particular glycosylated proteins, or glycosylation patterns of polypeptides. Other structures which may represent a tumor-associated antigen are, e.g., glycolipids. These include, for example, gangliosides, such as GM2. Moreover, tumor-associated antigens may be represented by changes in the composition of lipids of the cell membrane which may be characteristic of cancer cells.

Examples of tumor-associated antigens are N-CAM, the Lewis Y carbohydrate antigen, CEA and Ep-CAM, which have already been mentioned above. Further examples are Sialyl Tn carbohydrate, Globo H carbohydrate, gangliosides such as GD2/GD3/GM2, Prostate Specific Antigen (PSA), CA 125, CA 19-9, CA 15-3, TAG-72, EGF receptor, Her2/Neu receptor, p97, CD20 and CD21. Monoclonal antibodies directed against all these antigens are available. Further tumor-associated antigens are described, e.g., in DeVita et al. (Eds., "Biological Therapy of Cancer", 2. Edition, Chapter 3: Biology of Tumor Antigens, Lippincott Company, ISBN 0-397-51416-6 (1995)).

The term "antibody" relates to antibodies of all possible types, in particular to polyclonal or monoclonal antibodies or also to antibodies produced by chemical, biochemical or gene technological methods. Methods for producing such molecules are known to the person skilled in the art. The way of producing the antibody is not important. Only its binding specificity for a relevant epitope of a cellular membrane antigen is important. Preferably, monoclonal antibodies are used, most preferably monoclonal antibodies of animal origin, in particular of murine origin. It is particularly preferred that the murine monoclonal antibody HE-2 is used, which can be produced as described, or an antibody which has the same fine specificity of binding as HE2.

Within the meaning of the present invention, the term "antibody" also includes fragments and derivatives of antibodies wherein these fragments or derivatives recognize a TAA. The therapeutically effective immune response which is induced by the vaccination with suitable antibodies directed against TAA is determined by the binding region of these antibodies, i.e. by their idiotype. Therefore, it is, in principle, also possible to use, instead of intact antibodies, fragments or derivatives of these antibodies for a successful vaccination as long as these derivatives still contain the idiotype of the respective starting-antibody. As examples, without being limiting, can be listed: F(ab)'$_2$ fragments, F(ab)' fragments, Fv fragments which can be produced either by known biochemical methods (enzymatic cleavage) or by known methods of molecular biology. Further examples are derivatives of antibodies, which can be produced according to known chemical, biochemical or gene technological methods. In this context, the term "derivative", in particular, also includes products which can be produced by chemical linkage of antibodies (antibody fragments) with molecules which can enhance the immune response, such as tetanus toxoid, Pseudomonas exotoxin, derivatives of Lipid A, GM-CSF, IL-2 or by chemical linkage of antibodies (antibody fragments) with lipids for a better incorporation into a liposome formulation. The term "derivative" also includes fusion proteins of antibodies (antibody fragments), which have been produced gene technologically, with polypeptides which can enhance the immune response, such as GM-CSF, IL-2, IL-12, C3d etc. According to the invention, the antibodies can, of course, also be applied in combination with each other. This means that two or more antibodies which recognize different membrane antigens or different epitopes of the same membrane antigen can be administered. The different antibodies can be administered simultaneously (together or separately) or subsequently. Cancer cells often express several TAA at the same time against which suitable antibodies for vaccination are either available or can be generated. In order to obtain an enhanced or possibly synergistic effect of the induced immune response and to minimize the potential danger of the selection of antigen-negative variants and in order to counteract a possible tumor cell heterogenity, it may be advantageous to use a combination of two or more suitable antibodies or their fragments or derivatives simultaneously for vaccination.

In the context of the present invention the term "vaccination" means an active immunization, i.e. an induction of a specific immune response due to administration (e.g. subcutaneous, intradermal, intramuscular, possibly also oral, nasal) of small amounts of an antigen (a substance which is recognized by the vaccinated individual as foreign and therefore immunogenic) in a suitable immunogenic formulation. The antigen is thus used as a "trigger" for the immune system in order to build up a specific immune response against the antigen. In principle, the required amounts of the antigen can be very small (some vaccines only contain about 5-10 µg antigen per dose of vaccination).

It is characteristic of an active immunization that dose-effect curve depends, over a wide range, only little on the amount of antigen administered. This means that the immune response is more or less identical in a wide range of doses. As a consequence, in the case of vaccination, the desired effect, i.e. the induction of an immune response, can already be achieved with very small amounts of antigen. It can, however, also be achieved in a comparable manner using substantially larger amounts of antigen. It is, of course, desirable to use, in general, as low a dosage as possible, in particular in view of side effects, costs for material etc., which are of importance as regards vaccination.

In the sense of the present invention a vaccination can, in principle, be either carried out in the therapeutic sense as well as in the prophylactic sense (as is the case with all antimicrobial vaccines). This means that the vaccination against cancer according to the present invention can be understood as both a therapeutic and a prophylactic application. Accordingly, it might optionally be possible to achieve a prophylactic protection against the breakout of a cancer disease by vaccination of individuals who do not suffer from cancer. Individuals to whom such a prophylactic vaccination can be applied are individuals who have an increased risk to develop a cancer disease, although this application is not limited to such individuals.

The use according to the present invention differs substantially from the basic possibilities of therapeutic application of antibodies for the treatment of cancer that have been known so far and have been described earlier and allows for an unexpectedly efficient treatment.

The binding region of an antibody against a TAA can represent a structural complementary picture of the binding epitope of the respective TAA according to the "lock and key" principle. This means that such an antibody has, in its idiotype, a structural information of the epitope of the TAA against which it is directed. Thus, if a cancer patient is vaccinated with a suitable immunogenic antibody against a TAA (i.e. for example with a murine MAB against a TAA), antibodies are produced in the patient which, in part, are directed against the idiotype of the antibody used as vaccine and which can structurally mimic the epitope of the TAA according to the "lock and key" principle. This means that due to such a vaccination, so to say, soluble variants of the epitope of the TAA are generated in the cancer patient, which can be effective as actively induced autologous antibodies for a long period of time and the titer of which can be boosted in suitable intervals by repeated vaccinations.

In a preferred embodiment, the human cellular membrane antigen is a structure which plays a role in adhesion processes. In this context, adhesion processes preferably are cell-cell-interactions wherein ligands or receptors on the cell surface are involved. Thus, adhesion molecules are ligands or receptors on the cell surface which serve the function of cell-cell-interaction. A subgroup of such adhesion molecules are the self-adhesion molecules. These possess the property to be able to bind to themselves.

The physiological effect of an immune response induced by vaccination with an antibody directed against a TAA naturally depends on the function of the respective TAA. If the TAA has, for example, the function of a receptor for the adhesion of tumor cells, in particular to a ligand on endothelial cells of the vascular system (such a property is important for the ability of the disseminated tumor cells to exit from the vascular system and to settle in tissue in order to form a metastasis), this ability for adhesion is reduced by vaccination with a suitable antibody directed against this TAA, since induced antibodies, which will compete for the interaction of the TAA with its ligand as they mimic the TAA in soluble form, will be permanently present in the circulation and the tissue.

Generally spoken, it is possible, according to the explanations given above, to achieve by vaccination with suitable antibodies against TAA which have a function as regards the malignity of tumor cells, that the induced immune response interferes with the function of the TAA in its interaction with its ligand and hampers or prevents this interaction. This means that cancer cells can not or not sufficiently express properties which are important for the malignant phenotype, which makes it possible to slow down or stop the development of the disease and to suppress the development of metastases, in particular, at an early stage.

In a further preferred embodiment, the cellular membrane antigen is capable of self-adhesion, i.e. certain epitopes of the antigen are responsible for the homophilic binding to the same antigen on another cell. Examples of such antigens are, inter alia, N-CAM (Neuronal Cellular Adhesion Molecule), CEA (Carcino Embryonic Antigen) and Ep-CAM (Epithelial Cell Adhesion Molecule). Antibodies directed against epitopes of self-adhesion antigens which are involved in this function, can, as described above, contain a structural information complementary to such an epitope. By vaccination with such antibodies, it is thus possible, as described above, to induce the formation of antibodies which have the property of this self-adhesion in the binding reaction. This means that such induced antibodies can, in turn, bind to the self-adhesion antigen since in such a case receptor and ligand are identical. Thus, it is possible to induce an immune response by vaccination of cancer patients with suitable antibodies directed against self-adhesion antigens, wherein said immune response in turn directly binds to tumor cells and thereby triggers various therapeutic effects. On the one hand, the ability of self-adhesion, which is important to malignant cells, is blocked and, on the other hand, human effector functions such as complement-dependent lysis and/or lysis due to activation of cytotoxic effector cells, can be triggered by the binding of the induced antibodies to the tumor cells, which lead to the destruction of the tumor cells.

By all the above mentioned mechanisms and effects, the formation of new metastases can be suppressed and the dissemination of the disease can, at least, be slowed down thanks to vaccination of cancer patients with suitable antibodies against TAA. In early stages of the disease, for example after a successful operation of a primary tumor (adjuvant stage), remaining disseminated tumor cells are prevented from establishing themselves as new metastases due to such vaccinations. This allows to prolong the relapse-free survival period and therefore the overall lifetime of such patients. It may optionally be possible to obtain a lifelong protection against the formation of metastases due to such vaccinations and booster vaccinations which are carried out in suitable intervals. Of particular interest are vaccinations of cancer patients with suitable antibodies directed against a self-adhesion TAA since in these cases, as described above, it is possible to achieve an enhanced therapeutic effect due to an additional direct attack of the induced immune response on the tumor cells.

In a further preferred embodiment, the pharmaceutical composition prepared according to the use of the present invention contains at least one adjuvant commonly used in the formulation of vaccines apart from the antibody. It is possible to enhance the immune response by such adjuvants. As examples of adjuvants, however not being limited to these, the following can be listed: aluminium hydroxide (Alu gel), derivatives of lipopolysaccharides, Bacillus Calmette Guerin (BCG), liposome preparations, formulations with additional antigens against which the immune system has already produced a strong immune response, such as for example tetanus toxoid, Pseudomonas exotoxin, or constituents of influenza viruses, optionally in a liposome preparation, biological adjuvants such as Granulocyte Macrophage Stimulating Factor (GM-CSF), interleukin 2 (IL-2) or gamma interferon (IFNγ).

In another preferred embodiment, the pharmaceutical composition prepared according to the use of the invention is suitable for administration for vaccination in a dosage of 0.01 to 4 mg antibody, preferably of 0.5 mg.

The vaccination can be carried out by a single application of the above mentioned dosage. However, preferably the vaccination is carried out by repeated applications. The number of repetitions is in the range from 1 to 12 per year, more preferably in the range from 4 to 8 per year. The dosage can remain the same or can decrease.

Booster vaccinations can be carried out in regular intervals, in principle, lifelong. Suitable intervals are in the range from 6 to 24 months and can be determined by monitoring the titer of the induced antibodies (a booster vaccination should be carried out as soon as the titer of the induced antibodies has dropped significantly).

The administration of the antibody can be carried out according to methods known to the person skilled in the art. Preferably, the pharmaceutical composition containing the antibody is suitable for a subcutaneous, intradermal or intramuscular administration.

The present invention furthermore relates to the use of antibodies which recognize a tumor-associated antigen for the vaccination against cancer diseases as well as to a method for treating cancer diseases by vaccination, wherein one or more antibodies which recognize a TAA are administered to a patient in an amount sufficient for vaccination. For the definitions and the preferred embodiments the same holds true as already described above in connection with the use according to the invention.

The use of antibodies directed against TAA or of their derivatives or fragments as vaccines differs substantially from the known applications of such anti-TAA antibodies for the passive immunotherapy. Some essential advantages of the use according to the invention in comparison to the passive antibody immuno therapy are summarized as follows:

Antibodies Directed Against TAA for the Passive Immunotherapy of Cancer:
   high dosage (>100 mg/intravenous infusion)
   short effect due to elimination of the effective agent
   xenogenic antibody undesirable due to immunogenity
   the duration of the therapy is limited, in particular in the case of xenogenic antibodies, due to the induction of an immune response and the danger of anaphylactic reactions caused thereby in the case of repeated applications Antibodies Directed Against TAA for the Prophylactic and/or Therapeutic Vaccination Against Cancer:
   low dosage (<1 mg/vaccination; subcutaneous, intradermal or intramuscular injection)
   long lasting effect of the directly induced immune response
   xenogenic antibodies desirable since the effect is based on immunogenicity
   duration of the treatment unlimited (booster vaccinations are always possible)

In the following, experiments will be described which show that the vaccination with a certain murine MAB (HE2), which is directed against the self-adhesion TAA Ep-CAM, or the vaccination with its F(ab)'$_2$ fragment directly leads to the induction of antibodies which selectively bind on human tumor cells expressing this antigen. This shows, as an example but without any limitation, that an immune response which can have a therapeutic effect in cancer diseases is induced by vaccination with suitable antibodies directed against a self-adhesion TAA or with their derivatives which, at least, comprise the idiotype of the starting antibody.

For this purpose, the murine monoclonal antibody HE2 was generated according to described standard procedures of the hybridoma technology (see, e.g., H. Zola. Monoclonal Antibodies: A Manual of Techniques. CRC Press, Inc. ISBN 0-8493-6476-0; 1988). Balb/c mice were immunized with human colorectal cancer cells according to standard protocols. The spleen cells were fused with the mouse melanoma line P3X63Ag8 and hybridomas were selected which produce antibodies which selectively bind to human colorectal cancer cells but not to melanoma cells. Finally, a hybridoma was selected which secreted an IgG2a/kappa antibody. This antibody (HE2) binds to Ep-CAM as can be shown, e.g., by Western Blot analysis with membrane preparations from KATO IIII stomach cancer cells using a known anti-Ep-CAM antibody (KS1-4) as a comparison.

The amino acid sequences of the variable regions of MAB HE2 are as follows:

```
Heavy chain:
QVQLQQSGAELVRPGTSVKVSCKASGYAFTNYLIEW (SEQ ID NO: 1)
VKQRPGQGLEWIGVINPGSGGTNYNEKFKGKATLTA
DKSSSTAYMQLSSLTSDDSAVYFCARDGPWFAYWGQ
GTLVTVSA Light chain:
NIVMTQSPKSMSMSVGERVTLTCKASENVVTYVSWY (SEQ ID NO. 2)
QQKPEQSPKLLIYGASNRYTGVPDRFTGSGSATDFT
LTISSVQAEDLADYHCGQGYSYPYTFGGGTKLEIK
```

The figures show:

FIG. 3 shows the induction of an antibody immune response against HE2 after vaccination of goats with the F(ab)'2 fragment of HE2 as determined in an ELISA.

Figure 10:
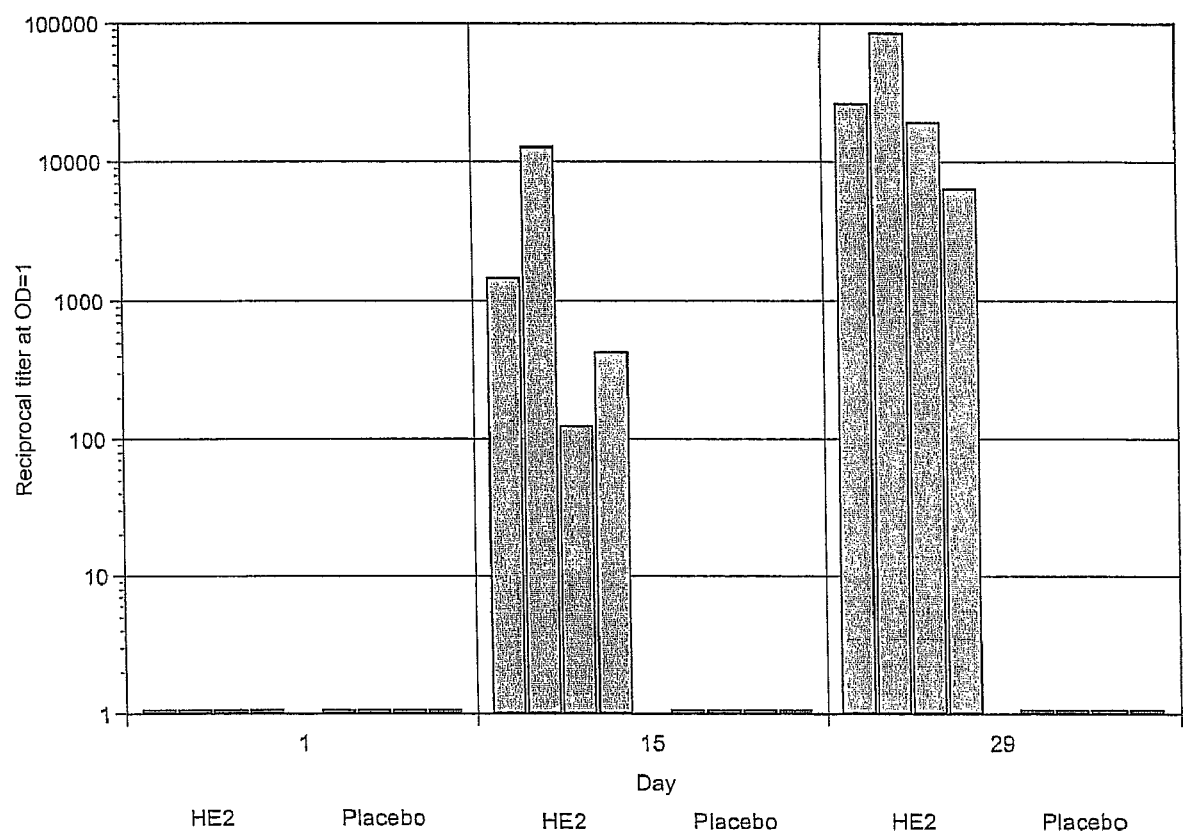

FIG. 10 shows the induction of an antibody immune response against HE2 detected in connection with a toxicity study with rhesus monkeys after vaccination of one group of rhesus monkeys with 0.5 mg HE2 adsorbed to aluminium hydroxide as well as the absence of an immune response against HE2 after treatment of another group of rhesus monkeys with an aluminium hydroxide formulation without antigen (placebo) as determined in an ELISA.

Figure 11:
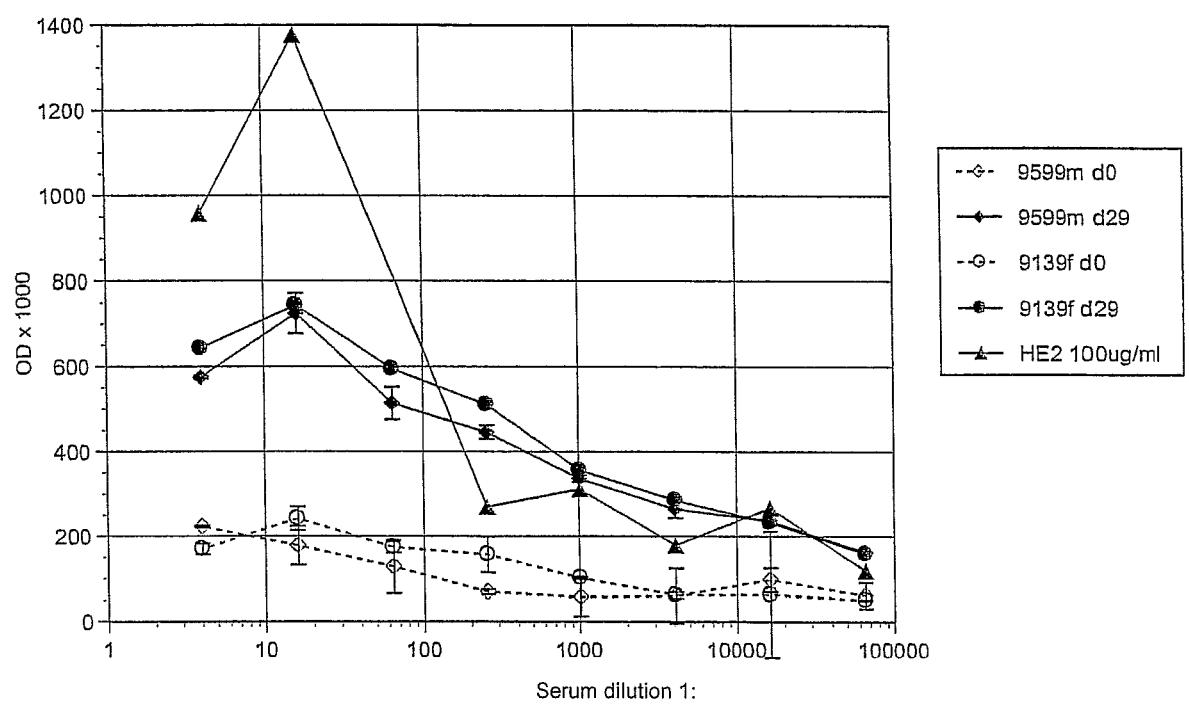

FIG. 11 shows exemplarily the induction of an antibody immune response against Ep-CAM positive human stomach cancer cells (Kato III) detected in connection with the toxicity study of rhesus monkeys with HE2 as determined in a cell-ELISA.

Figure 12:
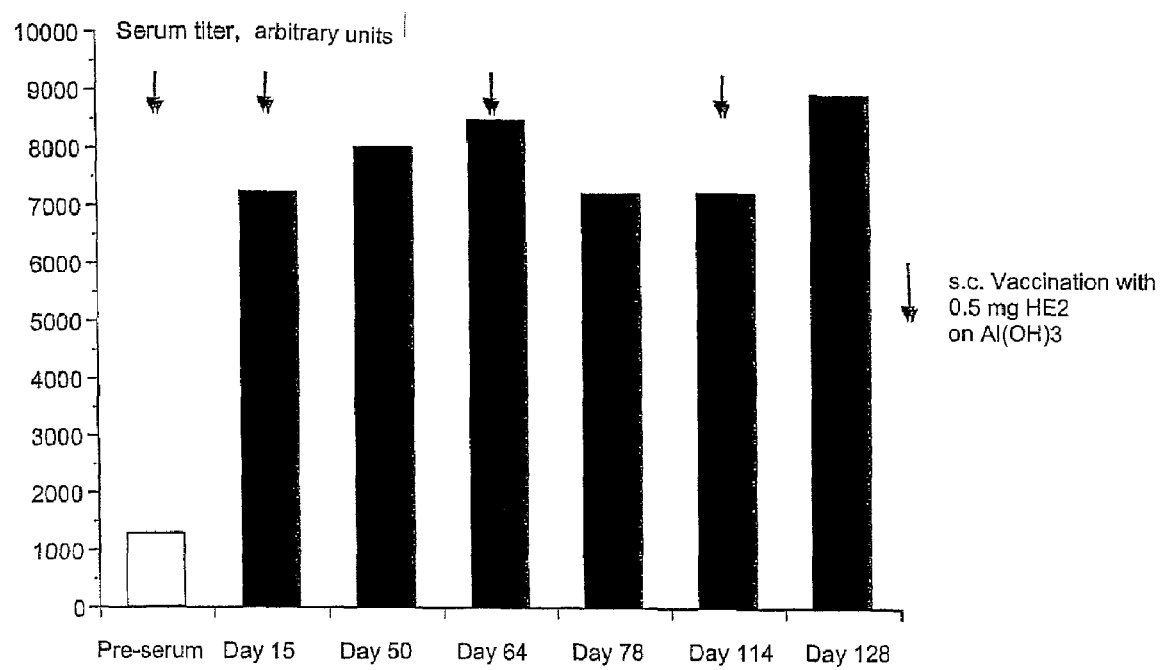

FIG. 12 shows the induction of an antibody immune response against Ep-CAM positive human stomach cancer cells (Kato III) after repeated vaccination of a patient suffering from intestinal cancer with 0.5 mg HE2 adsorbed to aluminium hydroxide, as determined in a cell-ELISA.

Figure 13:
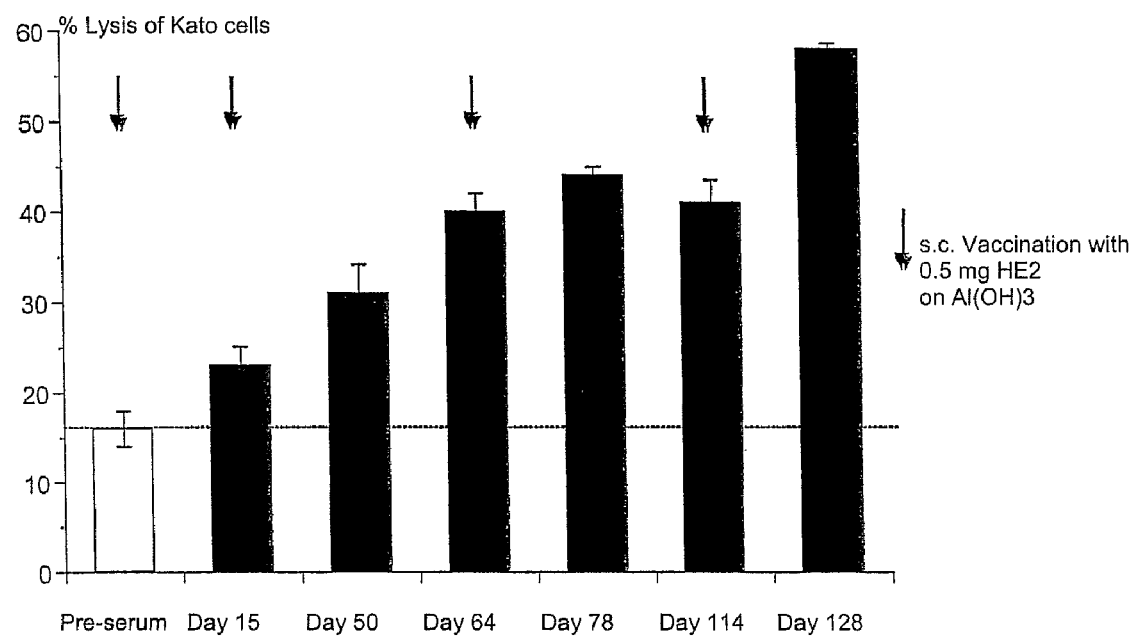

FIG. 13 shows the induction of a serum cytotoxicity against Ep-CAM positive human stomach cancer cells (Kato III) after repeated vaccination of a patient suffering from intestinal cancer with 0.5 mg HE2 adsorbed to aluminium hydroxide, as determined in a cell lysis experiment.

Figure 1:
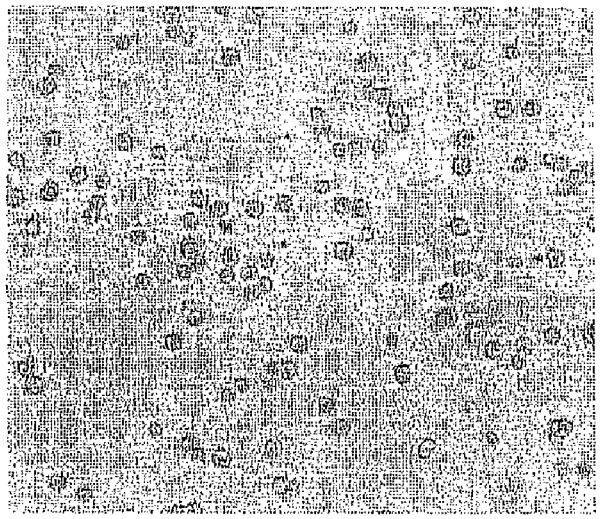
FIG. 1 shows the inhibition of the self-adhesion of the small cell lung cancer line SW2 by the MAB HE2 in vitro.
Figure 1:
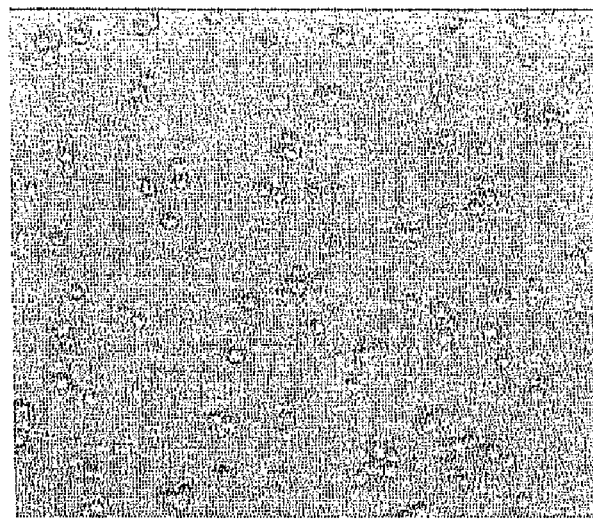
Figure 2:
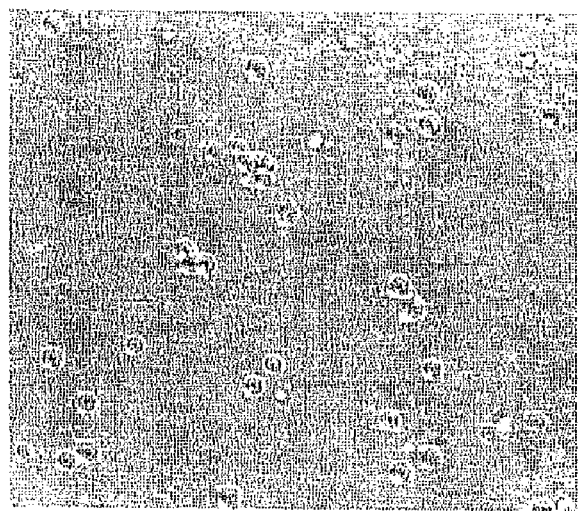
FIG. 2 shows the self-adhesion of the human small cell lung cancer line SW2 without the influence of the MAB HE2 in vitro as a control to the experiment shown in FIG. 1.
Figure 2:
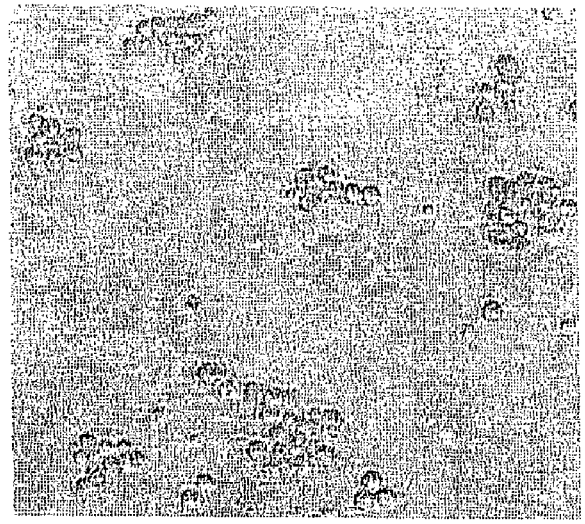

The following examples serve to further illustrate the invention but shall not limit it:

In order to show that the murine MAB HE2 binds to an epitope of the self-adhesion antigen Ep-CAM, which is involved in the homophilic binding, the influence of HE2 on the ability for self-adhesion of the human cell line SW2 was investigated. This small cell lung carcinoma line tends to form cell clusters in in vitro culture within several hours after preceding single seeding. The description of the experiment can be found in Example 1. As is evident from FIGS. 1 and 2, the formation of cell clusters is prevented to a large extend by the addition of HE2. This proves that HE2 binds to an epitope of Ep-CAM which is involved in the homophilic binding of this membrane protein.

In order to be able to investigate the direct humoral immune response to the vaccination with the F(ab)'$_2$ fragment of the murine MAB HE2, goats were immunized with this fragment. The fragment was prepared according to methods that are known and described by cleavage of HE2 with pepsin and was purified. The immunization of the goats is described in Example 2.

First, the goat immunoserum that was recovered and pooled was investigated, in comparison to a pre-serum, for immuno globulins which are directed against the MAB HE2 in order to determine the total immune response of the vaccinated goats. This investigation was carried out with the help of an ELISA assay, the experimental description of which is given in Example 3. The result of this experiment is shown in FIG. 3: the goats have, due to the vaccination with the F(ab)'$_2$ fragment of the MAB HE2, developed a strong immune response thereto, whereas no antibodies against HE2 could be found in the pre-serum.

Figure 4:
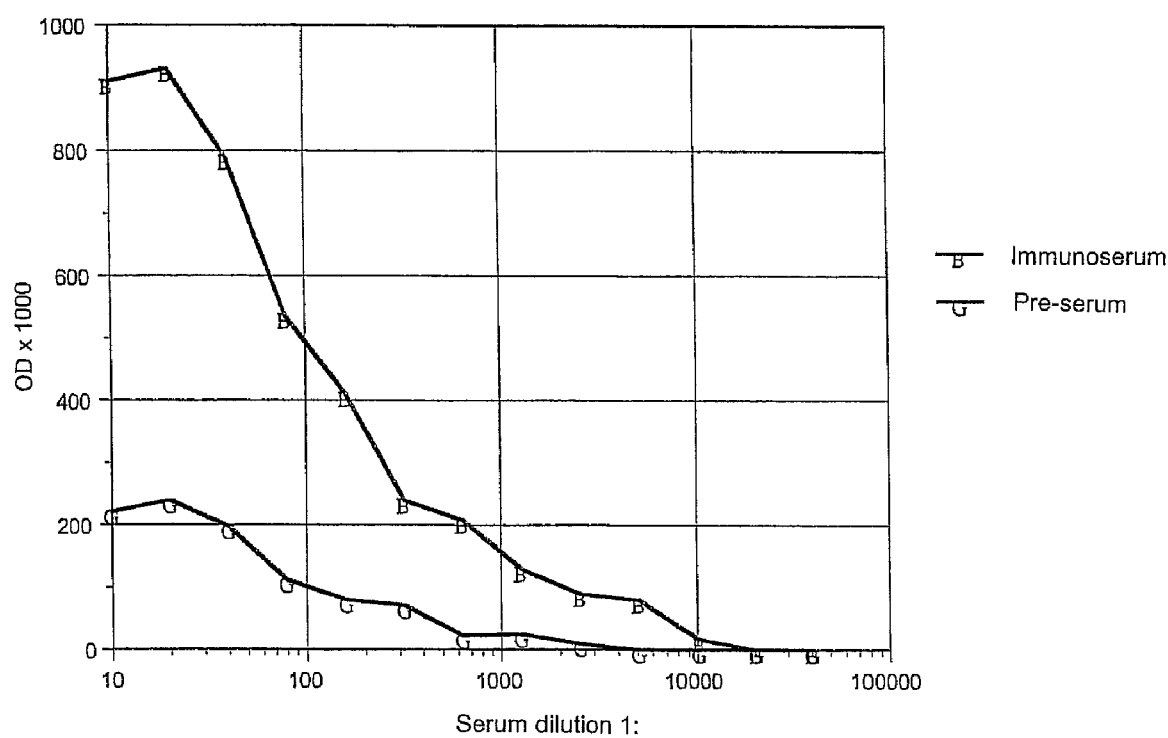
FIG. 4 shows the induction of an antibody immune response against Ep-CAM positive human stomach cancer cells (Kato III) after vaccination of goats with the F(ab)'2 fragment of HE2 as determined in a cell-ELISA.
Figure 5:
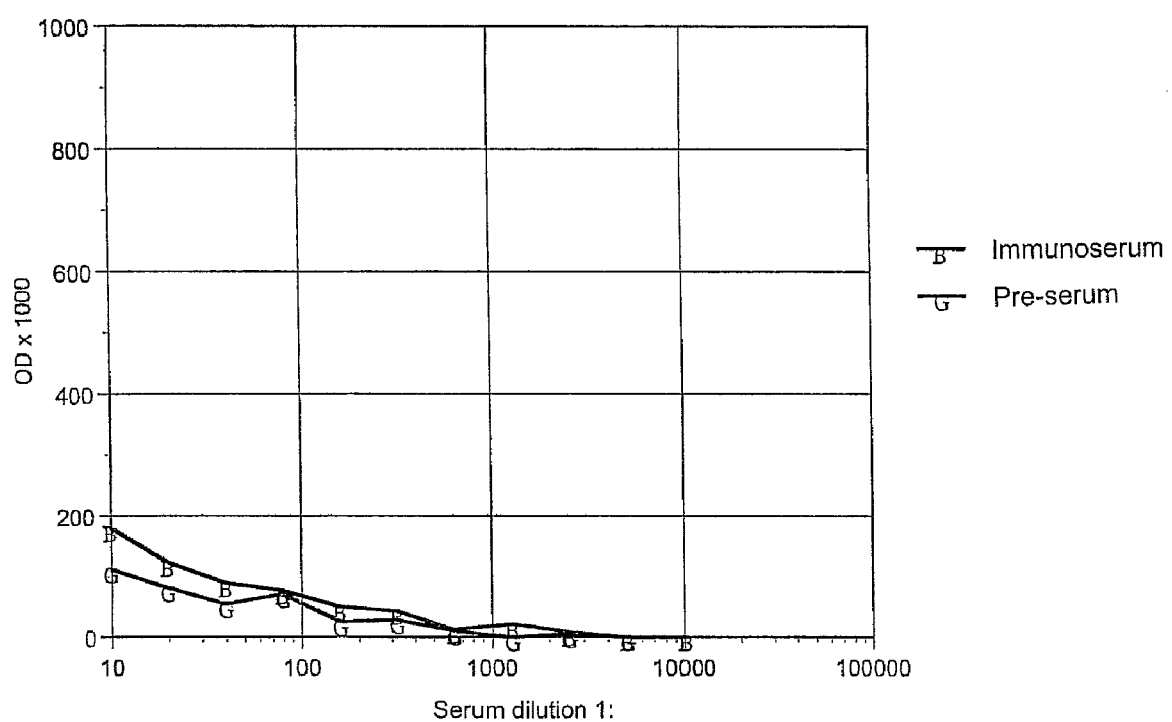
FIG. 5 shows the absence of an antibody immune response against Ep-CAM negative human melanoma cells (WM9) after vaccination of goats with the F(ab)'2 fragment of HE2 as determined in a cell-ELISA, which was carried out as a control to the experiment shown in FIG. 4.

In the following, it was investigated whether it is possible to detect immunoglobulins in the goat immunoserum, which bind to human cancer cells which express the TAA against which the MAB HE2 is directed (Ep-CAM). For this purpose, the stomach cancer cell line KATO III was used. Also the binding to a human cell line, which does not express Ep-CAM (WM9 melanoma cells), was tested as a control. These investigations were carried out with the help of cell-ELISA assays, the experimental description of which is given in Example 4. The results of these experiments are shown in FIGS. 4 and 5: the goat immunoserum contains immunoglobulins which strongly bind to the Ep-CAM positive KATO cells, whereas no binding can be detected on the Ep-CAM negative WM9 cells. The pre-serum contains no antibodies which bind to these cells. This very surprising result shows that antibodies generated by the vaccination with the HE2-F(ab)'$_2$ fragment are indeed capable to bind themselves again to cells which express the TAA recognized by HE2. Consequently, the function of the TAA of self-adhesion could be transferred to the antibodies which were generated by the vaccination with HE2, as previously described in detail.

In order to prove that the antibodies produced in the goats due to the vaccination with the F(ab)'$_2$ fragment of HE2 and which are directed against the idiotype of this MAB are indeed those which bind to the KATO cells, the anti-idiotypic portion of these induced antibodies was specifically purified from the goat immunoserum with the help of a sequence of immunoaffinity chromatographies as principally described (Proc. Natl. Acad. Sci. USA 81 (1984), 216). The sequence of the purification steps is again summarized in Example 5.

Figure 6:
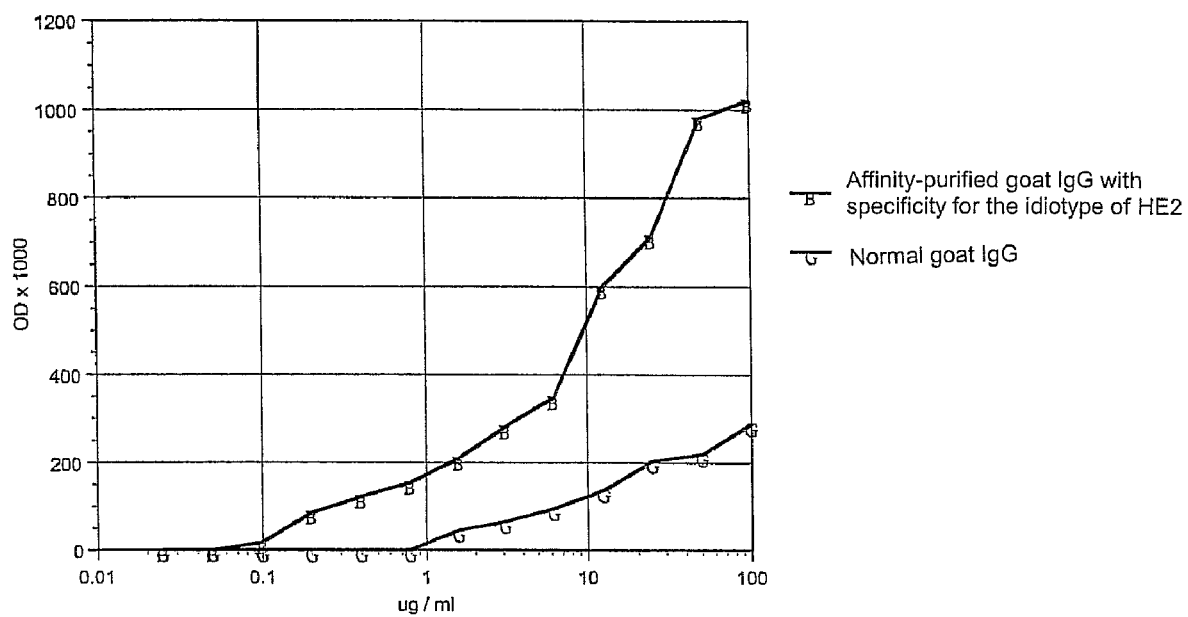
FIG. 6 shows the binding of an affinity purified antibody fraction from serum of goats, which were vaccinated with the F(ab)'2 fragment of HE2, to Ep-CAM positive human stomach cancer cells (Kato III) as determined in a cell-ELISA.
Figure 7:
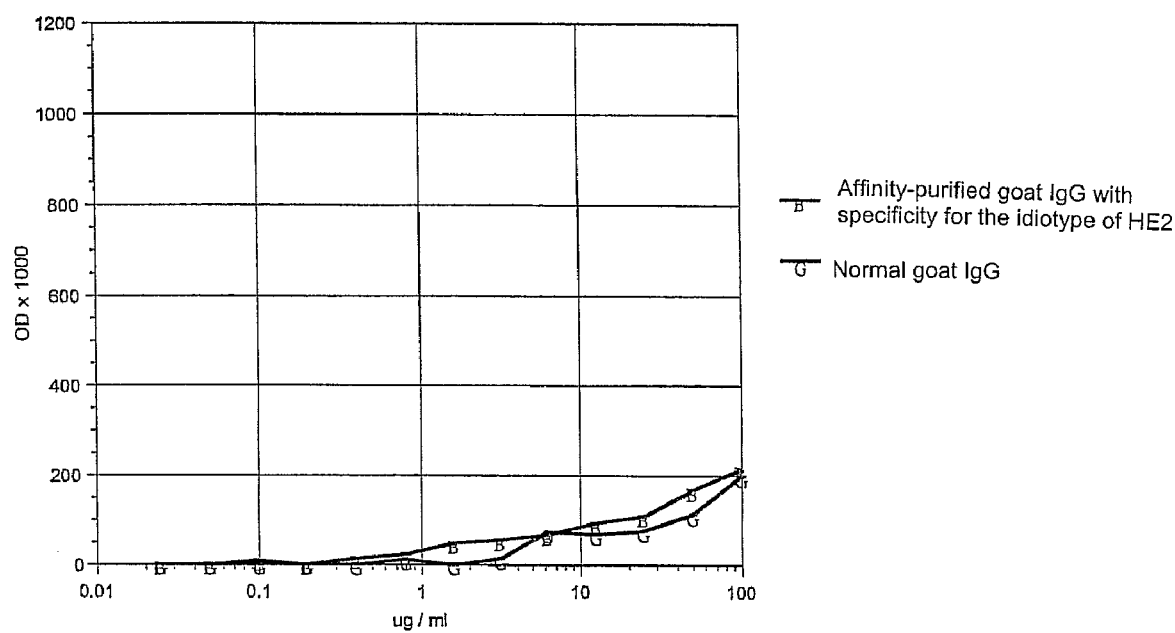
FIG. 7 shows the absence of the binding of an affinity purified antibody fraction from serum of goats, which were vaccinated with the F(ab)'2 fragment of HE2, to Ep-CAM negative human melanoma cells (WM9) as determined in a cell-ELISA, which was carried out as control to the experiment shown in FIG. 6.

These affinity purified goat antibodies were again tested for their binding to the Ep-CAM positive KATO cells as well as to the Ep-CAM negative WM9 cells. The experimental description is given in Example 6. The result of these experiments is shown in the FIGS. 6 and 7: the goat IgG, which is directed against the idiotype of HE2, binds strongly to the Ep-CAM positive KATO cells, whereas unspecific goat IgG hardly binds. The binding of the affinity purified specific goat IgG to the Ep-CAM negative WM9 cells, however, does not differ from that of the unspecific goat IgG. It is thus proven that the fraction of the antibodies which directly developed due to the vaccination with the F(ab)'$_2$ fragment of HE2 and which are directed against the idiotype of this antibody, contains the antibodies which bind to the cancer cells which express the TAA recognized by HE2. By this experiment it is also conclusively shown that the antibodies against Ep-CAM positive cells induced by the vaccination with HE2 are not the result of a double autologous idiotypic network cascade as was postulated in several publications (see, e.g.: Cancer Immunol. Immunother. 42 (1996), 81-87), for such anti-idiotypic antibodies (Ab3) could not at all be purified by affinity chromatography on an Ab1 (=HE2) column since, according to the idiotypic network, they cannot bind to Ab1 but only to Ab2.

In view of the above described results of the immunization of goats with the F(ab)'$_2$ fragment of HE2, vaccination studies were also carried out with rhesus monkeys in order to confirm the immunological results in a species closely related to human. For these experiments, the complete murine MAB HE2 was used as immunogen. It was assumed that the murine Fc part as a large xenogeneic protein would also enhance the immune response against the idiotype (carrier effect). In order to avoid possible local side effects, aluminium hydroxide was used as a mild adjuvant. The preparation of the formulation for these vaccination experiments is described in Example 7.

The formulation described in Example 7 was injected subcutaneously in the back of four rhesus monkeys (0.5 mg HE2=0.5 ml per vaccination, administered two times at an interval of four weeks). For the recovery of serum, blood was taken at several points of time.

Figure 8:
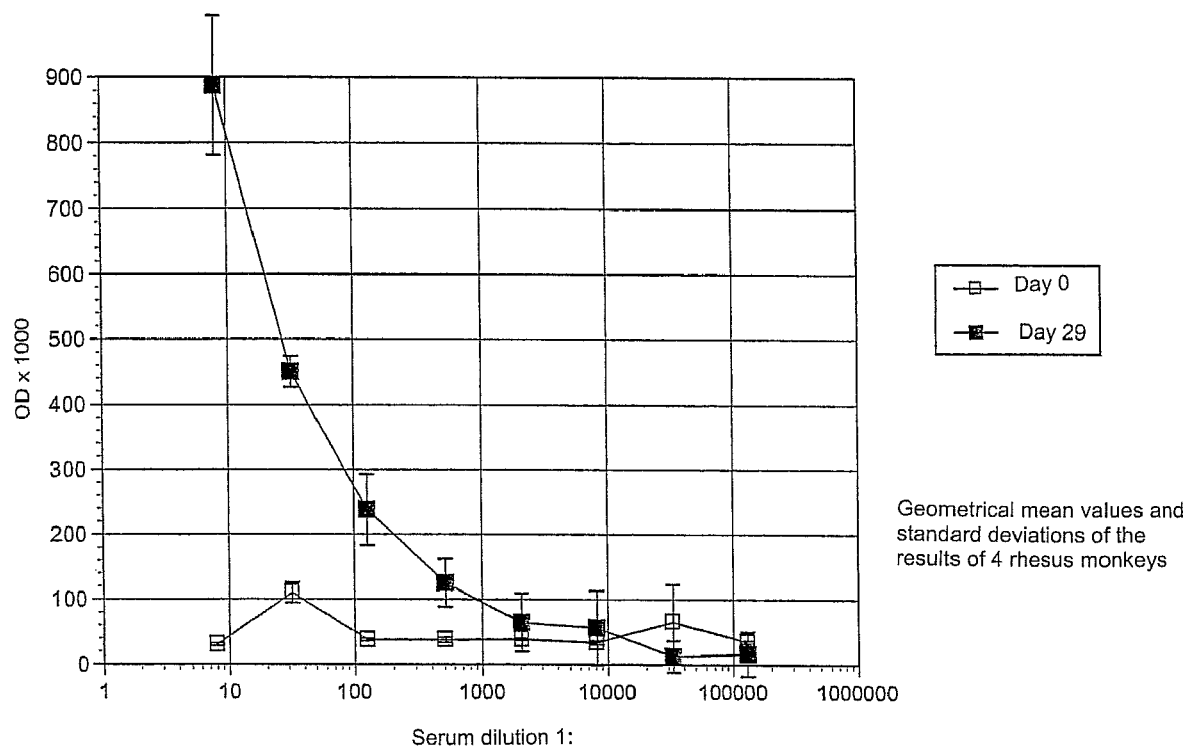
FIG. 8 shows the induction of an antibody immune response against HE2 after vaccination of rhesus monkeys with 0.5 mg HE2 adsorbed to aluminium hydroxide as determined in an ELISA.

First, the immune response against HE2 was determined in an ELISA. The experimental description is given in Example 8. As shown in FIG. 8, significant titers of antibodies against HE2 can already be measured on the day 29.

Figure 9:
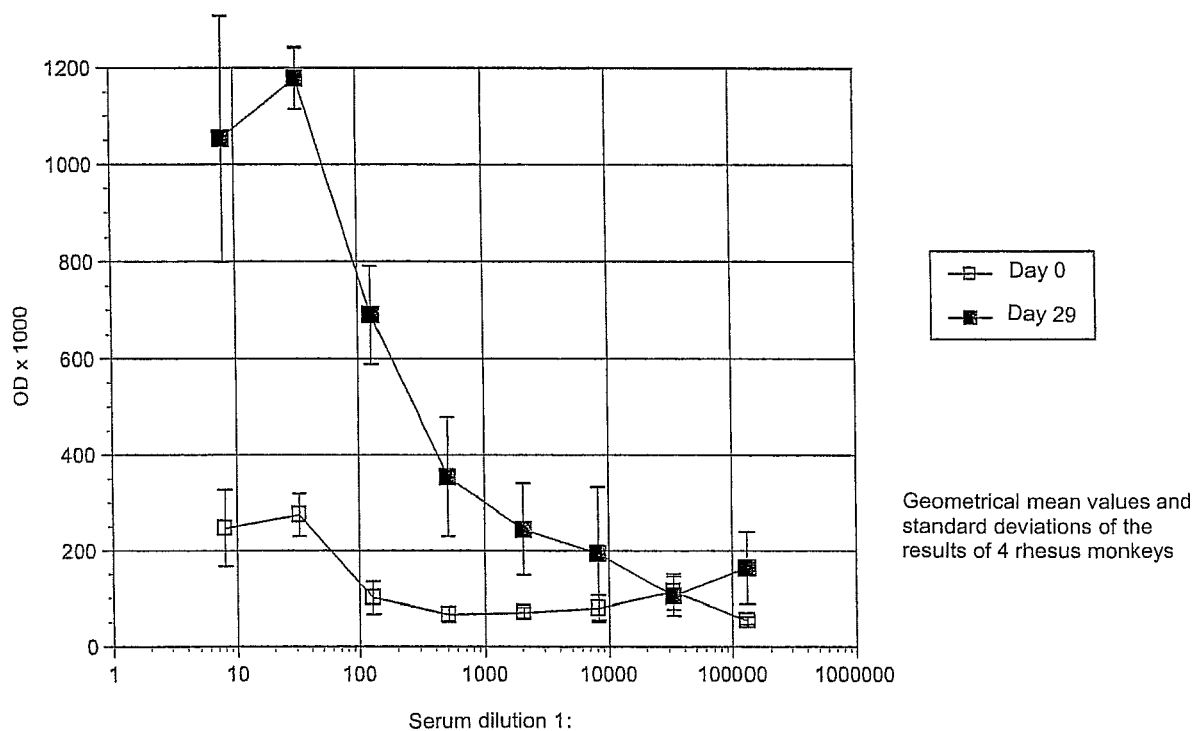
FIG. 9 shows the induction of an antibody immune response against Ep-CAM positive human stomach cancer cells (Kato III) after vaccination of rhesus monkeys with 0.5 mg HE2 adsorbed to aluminium hydroxide as determined in a cell-ELISA.

It was furthermore investigated whether antibodies are induced by the vaccination which bind to KATO III cells. For these tests, a cell-ELISA was used. The experimental description is given in Example 9. As shown in FIG. 9, antibodies which bind to Ep-CAM positive Kato III tumor cells are already induced on day 29 in all animals.

In the following, four animals were vaccinated with HE2 adsorbed to aluminium hydroxide in connection with a toxicity study with rhesus monkeys. Four other rhesus monkeys received aluminium hydroxide as a placebo. The preparation of the formulations is described in Examples 10 and 11. In total, the rhesus monkeys were injected subcutaneously in the back four times with 0.5 ml of the respective formulation (effective agent or placebo) (days 1, 15, 29 and 57). For the recovery of serum, blood was taken before the start of the study and at different times during the treatment.

Again, the immune response against HE2 was first determined in an ELISA. The experimental description is given in Example 8. As shown in FIG. 10, all four rhesus monkeys of the HE2 group developed a significant humoral immune response against HE2 already after one vaccination which was further enhanced by the second vaccination, whereas the rhesus monkeys of the placebo group do not show any increase in the titer of antibodies against HE2.

These findings were further confirmed by immunoaffinity purification of the sera of day 43 of the monkeys of the HE2 group. The experimental description is given in Example 12. As shown in the following table, all four monkeys have developed a strong IgG immune response against HE2 (secondary immune response) in their serum on day 43, whereas the IgM portion is comparable to that of the pre-sera.

| monkey | day | μg/ml IgM against | μg/ml IgG against |
|--------|-----|-------------------|-------------------|
| 9206m  | −14 | 7.7               | 2.8               |
|        | 43  | 16.3              | 135.2             |
| 9599m  | −14 | 17.9              | 2.5               |
|        | 43  | 25.4              | 449.3             |
| 8415f  | −14 | 16.0              | 3.2               |
|        | 43  | 22.5              | 159.9             |
| 9139f  | −14 | 5.3               | 5.0               |
|        | 43  | 10.3              | 69.8              |

Also the induction of antibodies against Ep-CAM positive Kato III cells was investigated. Again, a cell-ELISA was used for these tests. The experimental description is given Example 9. As is shown exemplarily in FIG. 11, rhesus monkeys of the HE2 group developed antibodies against Kato III cells already on day 29.

In view of the above described results of the vaccination of goats and rhesus monkeys, a patient suffering from intestinal cancer with metastases (Dukes D) was in the following vaccinated with the MAB HE2, adsorbed to aluminium hydroxide, in an anecdotal case. The preparation of the formulation is described in Example 7. In total, the patient was injected four times (day 1, 50, 78, 114) subcutaneously in the upper extramities with 0.5 ml of this formulation (corresponds to 0.5 mg HE2). Blood was taken for the recovery of serum prior to each vaccination and on day 128. First, it was investigated whether antibodies were induced by the vaccination which bind to KATO III cells. The cell-ELISA was again used for these tests. The experimental description is given in Example 9. The results of these experiments are shown in FIG. 12 High titers of antibodies which bind to KATO III cells are obviously induced in this cancer patient due to the vaccination.

It was furthermore investigated whether the antibodies induced by the vaccination with HE2 mediate a cytotoxic effect against KATO III cancer cells ex vivo. For this purpose, KATO III cells were incubated with pre- and immunosera of this cancer patient in order to demonstrate a complement-dependent lysis mediated by the induced antibodies. The experimental description is given in Example 13.

The results are shown in FIG. 13. The antibodies induced by the vaccination with HE2 are obviously able to destroy Ep-CAM positive KATO III cells via complement-dependent lysis in autologous patient serum.

The above described experiments exemplarily show that the vaccination with suitable antibodies against a self-adhesion TAA, such as Ep-CAM, or their derivatives with the same idiotype as the respective starting antibodies, triggers a humoral immune response which selectively binds on tumor cells which express this self-adhesion TAA. The induced antibodies may display a cytotoxic potential against such tumor cells. A vaccination with such antibodies can therefore lead to a therapeutic effect in cancer diseases.

EXAMPLES

| Materials used: | |
|---|---|
| microtiter plates: | Immuno Plate F96 MaxiSorp (Nunc) for ELISA Cell Culture Cluster (Costar; Cat.Nr. 3598) for cell-ELISA |
| cell lines: | SW2: human small cell lung carcinoma line, Ep-CAM positive<br>KATO III: human stomach cancer cell line, Ep-CAM positive (ATCC HTB 103)<br>WM 9: human melanoma cell line, Ep-CAM negative |
| Coupling buffer: | 0.1 M NaHCO$_3$<br>0.5 M NaCl<br>pH value 8.0 |
| Purification buffer A: | PBS def<br>0.2 M NaCl<br>pH value 7.2 |
| Purification buffer B: | 0.1 M glycine/HCl<br>0.2 M NaCl<br>pH value 2.9 |
| Medium A: | RPMI 1640 + 2 g/l NaHCO$_3$<br>100 U/ml penicillin G |

-continued

| Materials used: | |
|---|---|
| | 100 µg/ml streptomycin sulfate<br>4 mM glutamine<br>10% fetal calf serum (heat inactivated) |
| Binding buffer: | 15 mM Na$_2$CO$_3$<br>35 mM NaHCO$_3$<br>3 mM NaN$_3$<br>pH value: 9.6 |
| PBS deficient: | 138 mM NaCl<br>1.5 mM KH$_2$PO$_4$<br>2.7 mM KCl<br>6.5 mM Na$_2$HPO$_4$<br>pH value: 7.2 |
| Fixing solution: | 0.1% glutardialdehyde in physiological NaCl solution |
| Washing buffer A: | 2% NaCl<br>0.2% Triton X-100<br>in PBS deficient |
| Washing buffer B: | 0.05% Tween 20 in PBS deficient |
| Blocking buffer A: | 5% fetal calf serum (heat inactivated) in PBS deficient |
| Blocking buffer B: | 1% bovine serum albumin<br>0.1% NaN$_3$<br>in PBS deficient |
| Dilution buffer A: | 2% fetal calf serum (heat inactivated) in PBS deficient |
| Dilution buffer B: | PBS deficient |
| Staining buffer: | 24.3 mM citric acid<br>51.4 mM Na$_2$HPO$_4$<br>pH value: 5.0 |
| Substrate: | 40 mg o-phenylen diamin dihydrochloride<br>100 ml staining buffer<br>20 µl H$_2$O$_2$ (30%) |
| Stop solution: | 4 N H$_2$SO$_4$ |

Example 1

In vitro cultivated SW2 cells are centrifuged and the pellet is suspended in Medium A and adjusted to $7 \times 10^4$ cells/ml. In the chambers of a LabTek either 0.1 ml PBS def are mixed with 0.3 ml of the cell suspension or 0.1 ml PBS def are mixed with 40 µg HE2 and then with 0.3 ml of the cell suspension (final concentration of HE2 100 µg/ml). Just before the cell suspension is added as the last constituent, the cells are separated with the pipette. Immediately after mixing, the respective cell suspensions are photographed in the inverted microscope (magnification 100-fold). Subsequently, the cell suspensions are cultivated for 4 hours at 37° C./5% CO$_2$ and then photographed again.

Example 2

Two goats are each vaccinated intradermally at multiple sites with 1.5 mg of the F(ab)'$_2$ fragment in 3 ml PBS deficient together with 3 ml of Freund's Complete Adjuvant (Difco). On day 8, a first booster vaccination as on day 1 is given, however with Freund's Incomplete Adjuvant (Difco). On day 29, a second booster vaccination is given in the same manner. However, no adjuvant is added. Blood is taken before the start of the vaccination and on day 54 for the recovery of serum for the analysis of the immune response developed.

Example 3

100 µl aliquots of the MAB HE2 (solution with 10 µg/ml in binding buffer) are incubated in the wells of a microtiter plate for 1 hour at 37° C. After washing the plate with washing buffer A six times, 200 µl of the blocking buffer A are added to each well and the plate is incubated for 30 minutes at 37° C.

After washing the plate as described above, 100 µl aliquots of the goat sera to be tested are incubated in dilutions from 1:100 to 1:1 000 000 in dilution buffer A for 1 hour at 37° C. After washing the plate as described above, 100 µl of the peroxidase-conjugated rabbit anti-goat-Ig antibody (Zymed) are added to each well at a dilution of 1:1000 in dilution buffer A and are incubated for 30 minutes at 37° C. The plate is washed with washing buffer A for four times and twice with staining buffer. The binding of the antibody is detected by addition of 100 µl of the specific substrate to each well and the staining reaction is stopped after about 10 minutes by addition of 50 µl stop solution. The evaluation is carried out by measuring the optical density (OD) at 490 nm (wavelength of the reference measurement is 620 nm).

Example 4

The wells of a microtiter plate were incubated at +4° C. over night with 100 µl of a cell suspension of the cell line to be tested at a concentration of $2 \times 10^6$ cells/ml in medium A. After sucking off the supernatant, the plate is incubated with 50 µl fixing solution per well for 5 minutes at room temperature. After sucking off the supernatant, 200 µl blocking buffer B are added to each well and the plate is incubated for 1 hour at 37° C. After washing twice with 200 µwashing buffer B, 100 µl aliquots of the goat sera to be tested are incubated for 1 hour at 37° C. at dilutions of 1:10 to 1:100 000 in dilution buffer B. After washing the plate twice with 100 µl ice-cold washing buffer B, 100 µl of the peroxidase-conjugated rabbit anti-goat-Ig antibody (Zymed) are added at a dilution of 1:1000 in dilution buffer A and are incubated for 45 minutes at 37° C. The plate is washed three times with 100 µl ice-cold washing buffer B. The binding of the antibody is detected by the addition of 100 µl of the specific substrate per well and the staining reaction is stopped after about 10 minutes by addition of 50 µl stop solution. The evaluation is carried out by measuring the optical density (OD) at 490 nm (wavelength of the reference measurement is 620 nm).

Example 5

The purification is principally described in Proc. Natl. Acad. Sci. USA 81:216, 1984 and is summarized as follows: in a first step, a purification of the total IgG contained in the goat serum is carried out according to known methods on a DEAE anion exchanger column. Subsequently, the goat antibodies which are directed against constant regions of the F(ab)'$_2$ fragment of HE2 are bound to an immunoaffinity column (CH-Sepharose 4B, Pharmacia) to which irrelevant murine IgG2a was coupled, whereas the fraction of the anti-idiotypic goat antibodies does not bind to this column. Therefore, in a last step, the flow-through of this immunoaffinity chromatography is bound to an immunoaffinity column (CH-Sepharose 4B, Pharmacia) to which HE2 was coupled. The fraction specifically bound to this column is eluted with a buffer pH 2.8 (0.1 M glycine/HCl) and neutralized. The goat IgG fraction obtained in this way is directed against the idiotype of HE2.

Example 6

This cell-ELISA is basically carried out in the same way as described in Example 4. Instead of serum dilutions, concentrations of 100 µg/ml to 0.031 µg/ml of the immunoaffinity-purified goat IgG and of the unspecific purified goat IgG, respectively, are used.

Example 7

0.83 ml of a suspension of Alu-Gel (Alu-Gel S by Serva, 2% suspension, quality degree: adjuvant for the preparation of vaccines) is carefully agitated for 1 hour at room temperature under sterile conditions with 0.5 ml of a solution of 10 mg/ml HE2 in PBS pH 5.5 together with 3.67 ml PBS def. (final concentration of HE2: 1 mg/ml; Alu-Gel S: 0.33%). Then, the suspension is sterilly filled in injection vials at aliquots of 0.5 ml.

Example 8

This ELISA is basically carried out in the same manner as described in Example 3 with the exception that a peroxidase-conjugated goat-anti-human-Ig antibody (Zymed) is used for the detection of the bound rhesus monkey antibodies. With this reagent rhesus monkey antibodies can be detected in the same manner as human antibodies since the sequence homology of the constant regions of human antibodies and rhesus monkey antibodies is about 98%.

Example 9

This cell-ELISA is basically carried out in the same manner as described in Example 4 with the exception that a peroxidase-conjugated goat-anti-human-Ig antibody (Zymed) is used for the detection of the rhesus monkey antibodies (or the human antibodies) which are bound to the cells. A peroxidase-conjugated goat-anti-mouse-IgG antibody (Zymed) is used for the detection of the murine HE2 as a control.

Example 10

3.5 ml of a solution of HE2 (10 mg/ml in PBS def. pH=5.5) are mixed under sterile conditions with 0.35 ml of an aqueous thimerosal solution (10 mg/ml; Sigma) as well as with 27.25 ml physiological saline solution and added to 3.9 ml of an aluminium hydroxide suspension (3% in water; Alhydrogel, Superfos Biosector, Denmark) under careful agitation. 0.6 ml of the suspension obtained in this way are then filled into depyrogenated glass tubes under sterile conditions which are sealed with a rubber plug with an aluminium cap.

Example 11

The placebo formulation is prepared in the same manner as described in Example 10 with the exception that 0.35 ml physiological NaCl solution is used instead of the antibody solution and 3.5 ml PBS def pH=5.5 and instead of the thimerosal solution.

Example 12

1 g CH-Sepharose 4B (Parmacia) are suspended in 30 ml 1 mM HCl for 15 minutes. The gel is then washed on a filter of sintered glass AG3 with 1 liter 1 mM HCl and subsequently with 200 ml coupling buffer. 10 mg HE2 (stock solution 10 mg/ml) are dialyzed against about 0.5 liter coupling buffer. This solution is mixed with the gel suspension in a sealed container. A ratio of gel: buffer of 1:2 leads to a suspension suitable for the coupling. This suspension is agitated for 5.5 hours at room temperature. Subsequently, the excess of the ligand is removed by washing with 3×30 ml coupling buffer. Remaining reactive groups are blocked by a 1 hour incubation at room temperature with 1 M ethanol amine. The gel is then agitated for 1 hour at room temperature with 0.1 M Tris-HCl buffer pH=8. Finally, the gel is washed with 3 cycles of buffers with alternating pH. Each cycle consists of 0.1 M sodium acetate buffer pH 4 with 0.5 M NaCl, and subsequently 0.1 M Tris-HCl buffer pH 8 with 0.5 M NaCl. The gel is kept at 4° C.

The immunoaffinity purification of the antibody fraction directed against HE2 from the serum of the rhesus monkeys is carried out according to the following instructions: the immunoaffinity purification is carried out on the FPLC system (Pharmacia). 1 ml of the gel obtained according to the above instructions is filled into a Pharmacia HR5/5 column. 0.5 ml serum are diluted 1:10 with Purification buffer A. This solution is pumped over the column at a rate of 1 ml/minute and washed with purification buffer A until the UV basis line of the detector is reached again (280 nm). Bound immunoglobulines are then eluted with Purification buffer B and the fraction is immediately neutralized after desorption with 0.5 M $Na_2HPO_4$ and 0.02% $NaN_3$ are added. 50 µl of the antibody fraction purified in this way are analyzed on a size fractionation column (SEC, Zorbax 250 GF) and the portions of IgG and IgM are quantified. For the SEC 220 mM phosphate buffer pH 7+10% acetonitrile is used as an eluent. Human IgG and human IgM serve as standard for the SEC which were each chromatographed in several concentrations for establishing a standard calibration curve (peak area vs. concentration). The calculation of the IgG and IgM concentrations in the affinity purified antibody fractions from rhesus monkeys was carried out by linear regression using the standard curves. The concentrations are indicated as pg/ml of the used monkey serum.

Example 13

One day before carrying out the test, KATO III cells are transferred to fresh medium A and are kept at 37° C./5% $CO_2$ in a cell culture flask. On the next day, the cells are first labelled with $^{51}$chrome. 5×10$^6$ cells are incubated in 800 µl medium A at 37° C./5% $CO_2$ with 100 µCi $Na_2^{51}CrO_4$. Subsequently, the cells are washed with medium A and adjusted to a density of 2.5×10$^5$ cells/ml. 100 µl aliquots of this cell suspension are pipetted into the wells of a microtiter plate. 100 µl aliquots of the patient sera to be tested are added and incubated for 3 hours at 37° C./5% $CO_{O2}$ (the sera are stored at—80° C. and are thawed only once for this assay in order to avoid harming the activity of the complement). The supernatants are recovered by using a Skatron-Harvesting-Press and are measured in a gamma-counter. As a result, the values for the "experimental release" are obtained. For the determination of the "total release", the cells are treated as described above wherein serum is replaced by a solution of 2% SDS, 50 mM $Na_2CO_3$ and 10 mM EDTA. The values for the "spontaneous release" are obtained by replacing serum by medium A. The result is calculated as follows:

$$\% \, Lyse = \frac{\text{experimental release} - \text{spontaneous release}}{\text{total release} - \text{spontaneous release}} \times 100$$

The test is carried out 3 times and the mean value and the standard deviation of the single results are indicated.

The invention claimed is:

1. A pharmaceutical composition for treatment of cancer comprising at least one antibody directed against the cellular membrane antigen Ep-CAM and aluminum hydroxide, wherein said antibody contains the idiotype of the HE2 antibody, and is contained in a dosage range of 0.01 to 4 mg.

2. The pharmaceutical composition of claim 1, wherein said antibody is of animal origin.

3. The pharmaceutical composition of claim 1, wherein said antibody is a monoclonal antibody.

4. The pharmaceutical composition of claim 3, wherein said antibody is a murine monoclonal antibody, wherein the variable region of the heavy chain is the amino acid sequence as shown in SEQ ID NO: 1 and wherein the variable region of the light chain is the amino acid sequence as shown in SEQ ID NO: 2.

5. The pharmaceutical composition of any one of claims 1-3, wherein said antibody has the same fine specificity of binding as the antibody defined in claim 4.

6. The pharmaceutical composition of claim 1, wherein said antibodies are directed against different epitopes of the membrane antigen.

7. The pharmaceutical composition of claim 1, further comprising at least one vaccine adjuvant.

8. A pharmaceutical composition for treatment of cancer disease comprising a first antibody directed against the cellular membrane antigen Ep-CAM and aluminum hydroxide, wherein said first antibody is a murine monoclonal antibody, wherein the variable region of the heavy chain is the amino acid sequence as shown in SEQ ID NO: 1 and wherein the variable region of the light chain is the amino acid sequence as shown in SEQ ID NO: 2 and is contained in a dosage range of 0.01 to 4 mg.

9. The pharmaceutical composition of claim 8, wherein said antibody is of animal origin.

10. The pharmaceutical composition of claim 8, wherein said antibody is of monoclonal antibody.

11. The pharmaceutical composition of claim 8, further comprising at least a second antibody directed against a different membrane antigen or against a different epitope of said Ep-CAM membrane antigen.

12. The pharmaceutical composition of claim 8, further comprising at least one vaccine adjuvant.

13. The composition according to claims 1 or 8, further comprising at least one adjuvant selected from the group consisting of Bacillus Calmette Guerin, tetanus toxoid, Pseudomonas exotoxin, Granulocyte Macrophage Stimulating Factor, interleukin-2, gamma interferon, derivatives of lipopolysaccharides or combinations thereof.

14. A method of treating individuals with cancer or identified as being at risk of developing cancer comprising administering to a patient in need thereof the pharmaceutical composition of claim 1.

15. The method according to claim 14, wherein said pharmaceutical composition is administered by subcutaneous, intradermal or intramuscular injection.

16. A method of treating cancer disease comprising administering to a patient in need thereof the pharmaceutical composition of claim 8.

17. The method according to claim 16, wherein said pharmaceutical composition is administered by subcutaneous, intradermal or intramuscular injection.

18. The method according to claim 16, wherein said pharmaceutical composition is administered by subcutaneous, intradermal or intramuscular injection.

19. The method according to claims 16 or 17, wherein said dosage is 0.5 mg antibody.

* * * * *

UNITED STATES PATENT AND TRADEMARK OFFICE
CERTIFICATE OF CORRECTION

| | | |
|---|---|---|
| PATENT NO. | : 7,691,372 B2 | Page 1 of 1 |
| APPLICATION NO. | : 11/548269 | |
| DATED | : April 6, 2010 | |
| INVENTOR(S) | : Helmut Eckert et al. | |

It is certified that error appears in the above-identified patent and that said Letters Patent is hereby corrected as shown below:

Column 1, line 7, cancel the text beginning with "This application is a continuation" to and ending with "under 35 U.S.C. § 120." in column 1, line 10 and insert the following text:

-- This application is a Continuation of U.S. Application No. 09/889,300 filed on July 13, 2001 the entire contents of which are hereby incorporated by reference and for which priority is claimed under 35 U.S.C. § 120. U.S. Application No. 09/889,300 is the national phase application under 35 U.S.C. § 371 of PCT International Application No. PCT/EP00/00174 which has an International filing date of January 12, 2000, which designated the United States of America and to which priority for the present application is claimed under 35 U.S.C. § 120. This continuation application claims priority under 35 U.S.C. § 119 on Application No. 1999 0051/99 filed on January 13, 1999. --

Signed and Sealed this

Third Day of August, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 116
<212> TYPE: PRT
<213> ORGANISM: Mus musculus

<400> SEQUENCE: 1

```
Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Ser Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ala
            115
```

-continued

```
<210> SEQ ID NO 2
<211> LENGTH: 107
<212> TYPE: PRT
<213> ORGANISM: Mus musculus

<400> SEQUENCE: 2

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105
```